US012642774B2

(12) United States Patent
Algahtani et al.

(10) Patent No.: US 12,642,774 B2
(45) Date of Patent: Jun. 2, 2026

(54) METHOD FOR PRODUCING A CORE-SHELL CAPSULE FOR DELIVERING A THERAPEUTIC AGENT

(71) Applicant: NAJRAN UNIVERSITY, Najran (SA)

(72) Inventors: Mohammed Saeed N. Algahtani, Najran (SA); Mohammed Abdul Aleem, Najran (SA); Javed Ahmad, Najran (SA)

(73) Assignee: NAJRAN UNIVERSITY, Najran (SA)

( * ) Notice: Subject to any disclaimer, the term of this patent is extended or adjusted under 35 U.S.C. 154(b) by 568 days.

(21) Appl. No.: 18/157,132

(22) Filed: Jan. 20, 2023

(65) Prior Publication Data
US 2024/0245621 A1 Jul. 25, 2024

(51) Int. Cl.
*A61K 9/51* (2006.01)
*A61K 38/13* (2006.01)

(52) U.S. Cl.
CPC .......... *A61K 9/5192* (2013.01); *A61K 9/5123* (2013.01); *A61K 9/5146* (2013.01); *A61K 9/5176* (2013.01); *A61K 38/13* (2013.01)

(58) Field of Classification Search
CPC .. A61K 9/5192; A61K 9/5146; A61K 9/5176; A61K 38/13
See application file for complete search history.

(56) References Cited

U.S. PATENT DOCUMENTS

| | | | | |
|---|---|---|---|---|
| 10,278,922 B2 * | 5/2019 | Anderson | ........... | A61L 27/3804 |
| 11,045,426 B2 | 6/2021 | Albed Alhnan et al. | | |
| 11,253,481 B1 * | 2/2022 | Ahmed | ................... | A61K 31/64 |

FOREIGN PATENT DOCUMENTS

| | | | | |
|---|---|---|---|---|
| CN | 106265080 B | 12/2019 | | |
| CN | 112843022 A | 5/2021 | | |
| EP | 3 191 084 B1 | 11/2018 | | |
| TW | M502479 U | 6/2015 | | |
| WO | WO-2019025869 A1 * | 2/2017 | ........... | A61K 9/2893 |
| WO | WO-2017134418 A1 * | 8/2017 | ........... | A61K 9/2095 |
| WO | WO-2019198923 A1 * | 10/2019 | ............. | A61K 38/13 |

OTHER PUBLICATIONS

Translation of WO-2019198923-A1. Park. (Year: 2019).*

(Continued)

*Primary Examiner* — Jennifer A Berrios
*Assistant Examiner* — Chasity P Janosko
(74) *Attorney, Agent, or Firm* — Oblon, McClelland, Maier & Neustadt, L.L.P.

(57) ABSTRACT

A method for producing a core-shell capsule for delivering a therapeutic agent is provided. The method includes printing a composite material via a nozzle on a substrate while moving the nozzle in a pre-designed pattern to create the shell of a hollow capsule. The shell defines a cavity within the hollow capsule, and the shell has an opening at an apex of an outer surface of the shell. The method includes introducing a composition, in liquid form, containing the therapeutic agent at a temperature of at least 45° C. into the cavity of the hollow capsule via the opening of the shell, and naturally cooling the composition inside the shell to solidify the composition and adhere the composition to an inner surface of the shell thereby forming a core of the core-shell capsule.

13 Claims, 3 Drawing Sheets

100

102 — Print a composite material via a nozzle on a substrate while moving the nozzle in a pre-designed pattern to create the shell of a hollow capsule 104 — Introduce a composition, in liquid form, containing a therapeutic agent at a temperature of at least 45°C into the cavity of the hollow capsule via an opening of the shell 106 — Naturally cool the composition inside the shell to solidify the composition and adhere the composition to an inner surface of the shell, thereby forming a core of a core-shell capsule

(56) References Cited

OTHER PUBLICATIONS

Harald Rupp, et al., "3D Printing of Core-Shell Capsule Composites for Post-Reactive and Damage Sensing Applications", Advanced Materials Technologies, vol. 5, Issue 11, Sep. 21, 2020, pp. 1-8.

Sadikalmahdi Abdella, et al., "3D Printing of Thermo-Sensitive Drugs", Pharmaceutics, vol. 13, Issue 1524, Sep. 21, 2021, pp. 1-27.

Tatsuaki Tagami, et al., "Application of 3D printing technology for generating hollow-type suppository shells", International Journal of Pharmaceutics, vol. 589, Issue 119825, Nov. 15, 2020, 2 pages (Abstract only).

* cited by examiner

100

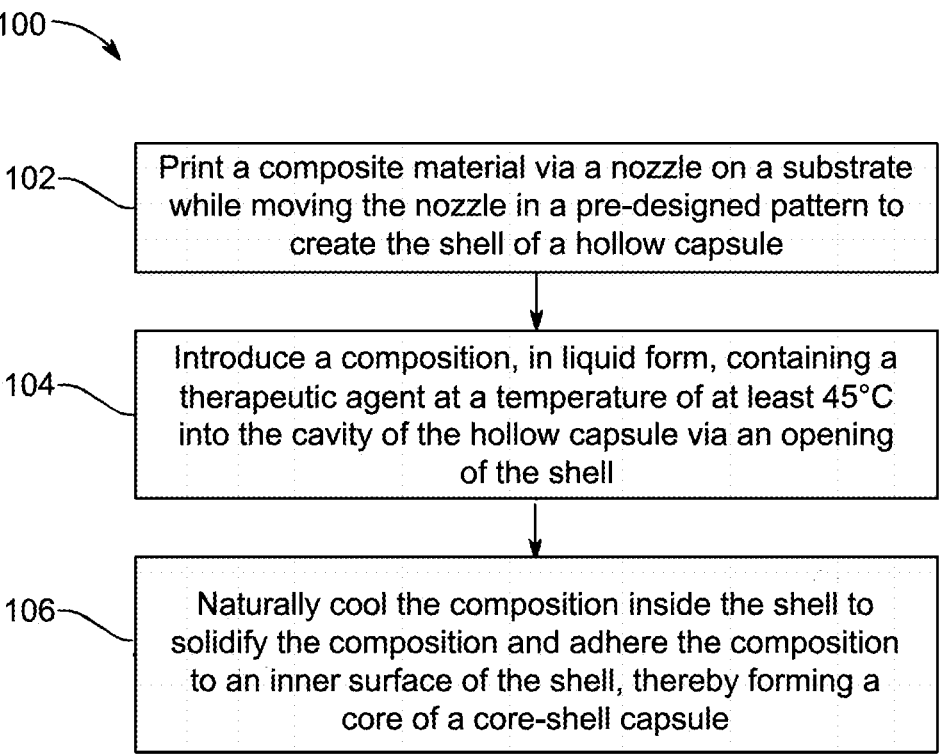

102
Print a composite material via a nozzle on a substrate while moving the nozzle in a pre-designed pattern to create the shell of a hollow capsule 104
Introduce a composition, in liquid form, containing a therapeutic agent at a temperature of at least 45°C into the cavity of the hollow capsule via an opening of the shell 106
Naturally cool the composition inside the shell to solidify the composition and adhere the composition to an inner surface of the shell, thereby forming a core of a core-shell capsule

FIG. 1

Dose = 25mg    Dose = 37.5mg    Dose = 50mg

METHOD FOR PRODUCING A CORE-SHELL CAPSULE FOR DELIVERING A THERAPEUTIC AGENT

BACKGROUND

Technical Field

The present disclosure relates to a method for producing a core-shell capsule, and more particularly, relates to a 3D printing method for producing a core-shell capsule for delivering a therapeutic agent.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Three-dimensional (3D) printing, also known as additive manufacturing, has come a long way since it was first developed. This technology has not only revolutionized multiple scientific and practical fields, including drug delivery, but also paved the way to develop pharmaceutical preparations that are difficult to produce by conventional methods. For example, Spritam® is the first tablet approved by Fused Deposition Modeling (FDM) in 2015 and manufactured using the 3D printing technology. This tablet has a high porosity and faster disintegration than tablets manufactured by traditional methods.

Fused deposition modeling (FDM), also known as fused filament fabrication (FFF), is a technique used for 3D printing. FDM works by laying down material layer by layer from a spool of material that is fed into a heated nozzle of a 3D printer to build a desired product on a substrate. FDM utilizes software that processes programs and includes mathematically slicing and orienting the model for building the product layer by layer. Support structures may also be built layer by layer using a second spool of material, for example, a soluble material may be provided on the second spool to build a soluble support structure. The material from the spool or spools feeds into the heated nozzle, which causes the material to become molten. Upon ejecting, the molten material immediately begins to harden.

Typically, materials suitable for 3D printing are polymeric materials with a glass transition temperature $T_g$ and/or a melting temperature $T_m$. Before the 3D printable material leaves the nozzle, the 3D printable material will be heated to a temperature of at least the glass transition temperature, and typically at least the melting temperature. Various materials may be used for FDM, including acrylonitrile butadiene styrene (ABS), polylactic acid (PLA), polycarbonate (PC), polyamide (PA), polystyrene (PS), lignin, rubber, carbon fibers, thermoplastics, polyphenylsufone, ultra high molecular weight polyethylene (UHMWPE), high impact polystyrene (HIPS), nylon, high density polyethylene (HDPE) eutectic materials, plasticine, room temperature vulcanization (RTV) silicone, etc. The material used is sometimes referred to as continuous fiber filament or a fiber tow.

Solid dosage forms (e.g., tablets, implants, etc.) are usually preferred relative to other formulations (e.g., injectable liquid formulations) due to storage stability, transportability, and ease of administration. However, the manufacturing of solid dosage formulation often involves sophisticated processing steps and large manufacturing facilities which inevitably rises cost of manufacturing and handling error. In addition, the marketed doses for the solid dosage forms are based on the one-size-fits-all method that does not keep pace with the steady progress in pharmacogenomics and personalized medicine. Thus, these manufacturing limitations have a detrimental impact on consumer choice and/or the customizability of healthcare products.

In the meantime, powder-based 3D printing has advanced to produce solid dosage forms with different drug release profiles. However, such techniques suffer from various shortcomings such as the need to dry the powders, extended processing times, weak tablets that disintegrate prematurely, poor resolution, poor shape control, and limited control of drug release profiles. In addition, powder-based 3D printing requires dedicated production areas for the manufacturing of predetermined doses, which makes it unsuitable to produce on-demand personalized doses and difficult to implement in the healthcare system. It is therefore desirable to develop solid dosage forms with accurate control of the drugs amount and customized release profiles.

Accelerated development in the field of pharmacogenetics and the relationship of a patient's profile to the extent of his/her response to pharmacological treatment has shown that drug strengths produced on a large scale is not always the best option for patients. Therefore, patients and healthcare professionals must make the best of the limited variety of dosages available, as dictated by the suppliers rather than a consumer's need. Large scale drug manufacturing thus often results in imbalanced therapeutic efficacy and increased side effects. Therefore, there is an urgent need to develop personalized medicine products that may best serve the patient and can overcome the limitations of the art.

In view of the forgoing, one objective of the present disclosure is to describe a method for producing a core-shell capsule for delivering a therapeutic agent. A further objective of the present disclosure is to provide a pharmaceutical formulation containing the core-shell capsule.

SUMMARY

In an exemplary embodiment, a method for producing a core-shell capsule for delivering a therapeutic agent is described. The method includes printing a composite material via a nozzle on a substrate while moving the nozzle in a pre-designed pattern to create the shell of a hollow capsule. The method also includes introducing a composition, in liquid form, containing the therapeutic agent at a temperature of at least 45° C. into the cavity of the hollow capsule via the opening of the shell, and naturally cooling the composition inside the shell to solidify the composition and adhere the composition to an inner surface of the shell thereby forming a core of the core-shell capsule.

In some embodiments, the shell defines a cavity within the hollow capsule, and the shell has an opening at an apex of an outer surface of the shell. In some embodiments, the shell of the hollow capsule is in the shape of an ovoid that widens from a top end to a bottom end opposite to the top end. In some embodiments, the average width of the opening is from about 1/20 to about 4/5 of an average maximum diameter of the shell. In some embodiments, during the printing, the substrate is supported on a movable stage. In some embodiments, the movable stage can move in multiple directions.

In some embodiments, the core is at least partially enclosed within the shell. In some embodiments, the concentration of the therapeutic agent in the core of the core-shell capsule and the concentration of the therapeutic agent in the composition in liquid form during introducing of the composition into the cavity of the hollow capsule are the same.

In some embodiments, the composite material includes a thermoplastic polymer having a glass transition temperature (Tg) of greater than or equal to 30° C.

In some embodiments, the composite material includes one or more thermoplastic polymers selected from the group consisting of a polyacrylate, a silicone, a polyurethane, a polyolefin, a polyalkylene glycol, a polyvinyl alcohol, a polyamide, an acrylonitrile butadiene styrene, a polylactic acid, a polyglycolide, a nylon, a co-polymer thereof and a mixture thereof.

In some embodiments, the composite material includes at least one plasticizer, and at least one filler.

In some embodiments, the printing is operated at a condition having a print speed in a range of 10 to 120 millimeters per second (mm/sec). In some embodiments, the printing is operated at a condition having a travel speed in a range of 10 to 200 mm/sec. In some embodiments, the printing is operated at a condition having a full density of at least 5%. In some embodiments, the printing is operated at a condition having at least one fill pattern selected from the group consisting of a linear fill pattern, a triangular fill pattern, a diagonal fill pattern, and a hexagonal fill pattern.

In some embodiments, the nozzle is operated at a temperature in a range of 50 to 400° C. In some embodiments, the nozzle has an output opening having a diameter in a range of 0.05 to 4 millimeters (mm).

In some embodiments, the movable stage is operated at a temperature of 30 to 120° C.

In some embodiments, the shell of the hollow capsule is printed via a fused deposition modelling (FDM) 3D printer.

In some embodiments, the FDM 3D printer has a communications interface coupled to a computing device, and the FDM 3D printer removably retains the computing device. In some embodiments, the computing device stores, retrieves, and processes the pre-designed pattern.

In some embodiments, the composition is introduced into the hollow capsule in a form selected from the group consisting of an emulsion, an oil solution, a dispersion, and a suspension.

In some embodiments, the composition includes at least one therapeutic agent and one or more pharmaceutically acceptable excipients or carriers.

In some embodiments, the composition is at least one liquid mixture selected from the group consisting of a self-nanoemulsified drug delivery system (SNEDDS), a self-microemulsifying drug delivery system (SMEDDS), and a self-emulsifying drug delivery system (SEDDS).

In some embodiments, the composition includes 0.0001 to 50 wt. % of at least one therapeutic agent, 15 to 55 wt. % of at least one emulsifier, 5 to 60 wt. % of at least one solvent, and 5 to 25 wt. % of at least one fatty acid, each wt. % based on a total weight of the liquid composition.

In some embodiments, the at least one emulsifier is selected from the group consisting of caprylate, a caprate monoglyceride, a caprate diglyceride, a glyceryl monocaprylate, a propylene glycol monocaprylate, a lauroyl glyceride, a stearoyl glyceride, a sorbitan monolaurate, a sorbitan monooleate, a sorbitan sesquioleate, a sorbitan trioleate, a glyceryl monostearate, a hydrogenated castor oil, a polysorbate, a polyethylene glycol, a polyethylene glycol ester, a glycerol ester, a polyvinylpyrrolidone, and a mixture thereof.

In some embodiments, the at least one solvent is selected from the group consisting of diethylene glycol monoethyl ether, polyethylene glycol 200, polyethylene glycol 400, polyethylene glycol 6000, propane-1,2,3-triol, polypropylene glycol, propylene glycol, 2-pyrrolidone, tetraethylene glycol, diethylene glycol monoethyl ether, and a mixture thereof.

In some embodiments, the at least one fatty acid is selected from the group consisting of heptanoic acid, octanoic acid, nonanoic acid, decanoic acid, and a mixture thereof.

In some embodiments, the composition includes 0.01 to 20 wt. % of cyclosporin A (CyA), 5 to 25 wt. % of propylene glycol monocaprylate, 10 to 30 wt. % of polyoxyl 35 hydrogenated castor oil, 1 to 20 wt. % of polyethylene glycol 400, 30 to 50 wt. % of polyethylene glycol 6000, and 5 to 25 wt. % of octanoic acid, each wt. % based on the total weight of the liquid composition.

In some embodiments, the method further includes mixing the composition, in liquid form, with water to form a nanoemulsion. In some embodiments, the nanoemulsion has an average particle size in a range of 10 to 800 nanometers (nm).

In some embodiments, the core-shell capsule stabilizes the therapeutic agent prior to administration and releases the therapeutic agents from the capsule following administration.

In some embodiments, a pharmaceutical formulation includes the core-shell capsule prepared by the method of the present disclosure. In some embodiments, the core-shell capsule contains an effective amount of the therapeutic agent to treat a subject.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 1 is a schematic flow chart of a method for producing a core-shell capsule for delivering a therapeutic agent, according to certain embodiments of the present disclosure;

DETAILED DESCRIPTION

Figures 2A, 2B, 2C, 2D, 2E, 2F:
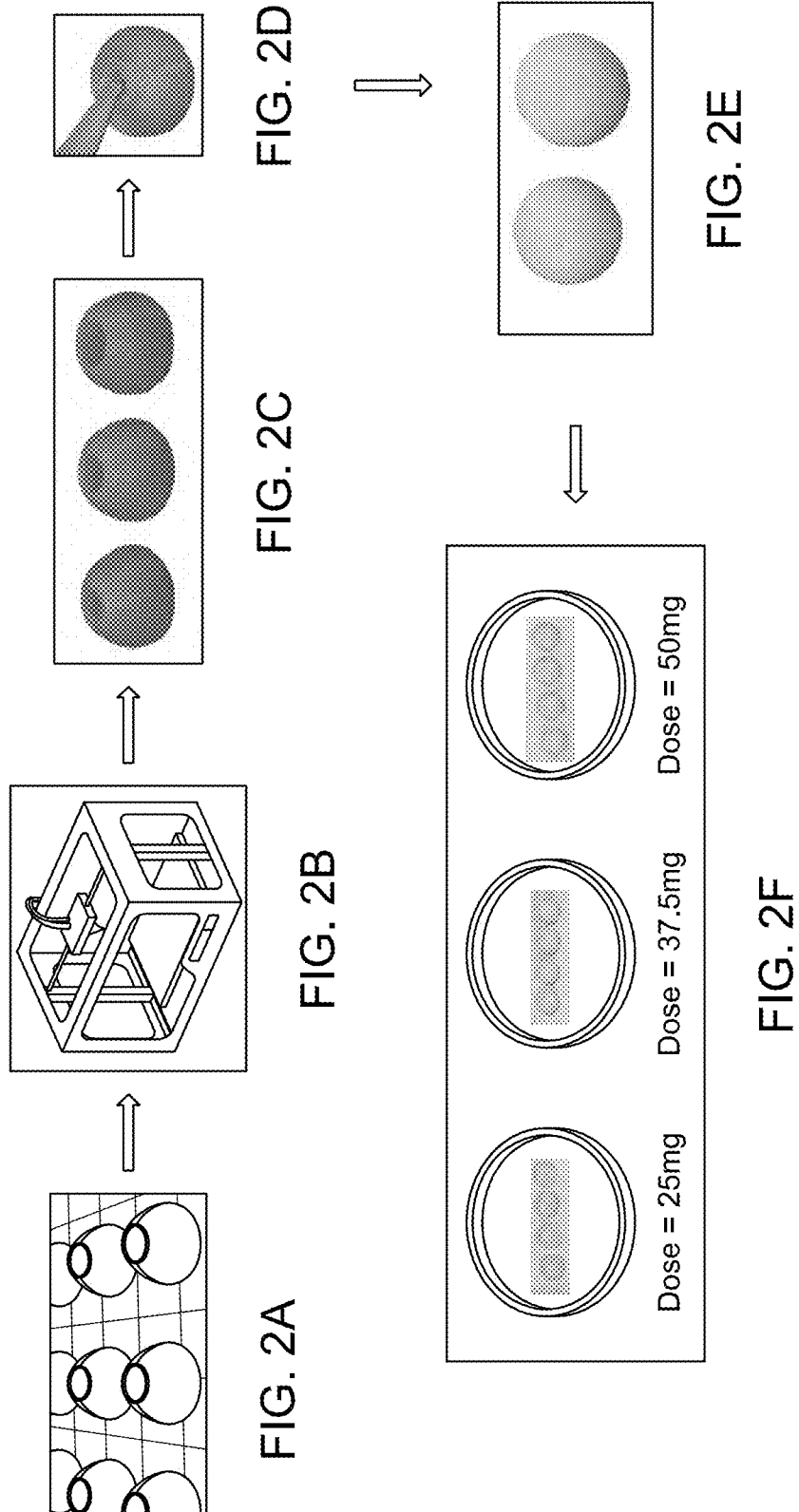
FIG. 2A is an AutoCAD design of the shell of the capsule, according to certain embodiments of the present disclosure.
FIG. 2B depicts an FDM printer, according to certain embodiments of the present disclosure.
FIG. 2C depicts printed shells of the capsules, according to certain embodiments of the present disclosure.
FIG. 2D illustrates the process of filling the shell of the capsule, according to certain embodiments of the present disclosure.
FIG. 2E illustrates the core-shell capsules, according to certain embodiments of the present disclosure.
FIG. 2F illustrates the core-shell capsules having different amounts of a therapeutic agent, according to certain embodiments of the present disclosure.

In the drawings, like reference numerals designate identical or corresponding parts throughout the several views.

Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

As used herein, the term '3D printing' refers to the method of creating a three-dimensional object layer-by-layer using a computer-created design. The method may include but is not limited to, selective laser sintering (SLS), fused deposition modeling (FDM) or fused filament fabrication (FFF), or stereolithography (SLA) using liquid materials, by melting or softening plastic materials and layered entity manufacturing (LOM). The printing method may depend on the materials used. A user may select a particular material according to the needs of the finished product and then select the 3D printing method according to the nature of the material to make the finished product.

As used herein, the term 'FDM 3D printing' refers to the technology that works both horizontally and vertically, where an extrusion nozzle moves over a build platform. The process involves the use of thermoplastic material that reaches a melting point and is then forced out, to create a 3D object layer by layer.

As used herein, the term 'emulsion' refers to the fine mixture of two naturally immiscible liquids, most commonly water and oil.

As used herein, the term 'dispersion' refers to the system in which distributed particles of one material are dispersed in a continuous phase of another material. The two phases may be in the same or different states of matter.

As used herein, the term 'suspension' refers to the heterogeneous mixture in which the solid particles are spread throughout the liquid without dissolving in it.

As used herein, the term 'therapeutic agent' refers to the chemical substance that is used for the treatment or mitigation of a disease condition or ailment.

As used herein, the term 'emulsifier' refers to the substance stabilizing an emulsion.

As used herein, the term 'fatty acid' refers to the carboxylic acid that is the structural component of several lipids. The fatty acid may be saturated or unsaturated. Most fatty acids are unbranched and contain an even number of carbon atoms. Unsaturated fatty acids have lower melting points than saturated fatty acids containing the same number of carbon atoms.

As used herein, the term 'thermoplastic polymer' refers to the plastic polymer material that becomes pliable or moldable at a certain elevated temperature and solidifies upon cooling.

As used herein, the term 'viscosity' refers to a viscosity determined by means of a Brookfield viscometer (UL adapter/30 rpm/20° C.) in accordance with testing protocols defined by Ph. Eur. 2.2.10 or USP <912> method II.

As used herein, the term 'glass transition temperature' refers to the temperature at which an amorphous polymer develops characteristic glassy-state properties such as brittleness, stiffness, and rigidity upon cooling. Glass transition temperature of materials described herein may be determined by a standard test method defined by ASTM E1640. Differential Scanning calorimetry (DSC) may also be utilized to measure the glass transition temperature of materials. For instance, glass transition temperatures may be discerned using the protocols set forth in ASTM E1356 and ASTM D7426.

As used herein, the term 'plasticizer' refers to the substance that is added to a material to make the substance softer and more flexible, to increase plasticity, to decrease viscosity, and to decrease friction during the manufacturing of the substance.

As used herein, the term 'self-nano emulsifying drug delivery system (SNEDDS)' refers to the anhydrous homogenous liquid mixture including oil, surfactant, drug, and co-emulsifier or solubilizer, which spontaneously forms oil-in-water nanoemulsion of approximately 200 nm or less in size upon dilution with water under gentle stirring.

As used herein, the term 'self-micro emulsifying drug delivery system (SMEDDS)' refers to the anhydrous homogenous liquid mixture including oil, surfactant, drug, and co-emulsifier or solubilizer, which spontaneously forms oil-in-water microemulsion upon dilution with water under gentle stirring.

As used herein, the term 'self-emulsifying drug delivery system (SEDDS)' refers to the kind of solid or liquid formulation composed of drugs, oil, surfactant, and co-surfactant.

As used herein, the term 'controlled release' refers to a release profile of a pharmaceutical composition, a therapeutic agent, and/or a chemical compound that conforms to a specific release pattern to produce a therapeutic outcome.

As used herein, the term 'enclose' means to seal, surround or enclose. When referring to a composition containing the therapeutic agent of the invention, encapsulation may be substantial, complete, or partial. The term 'substantially enclose,' 'substantially enclosed,' or 'substantially encapsulated' means that at least 50%, 60%, 70%, 80%, 85%, 90%, 95%, 96% or more of the composition containing the therapeutic agent can be sealed, enclosed or encased within the capsule. The term 'at least partially enclose,' 'at least partially enclosed,' or 'at least partially encapsulated' means that at least 50%, 60%, 70%, 80%, 85%, 90%, 95%, 96% or more of the composition containing the therapeutic agent can be sealed, enclosed or encased within the capsule. The term 'partially enclose,' 'partially enclosed,' or 'partially encapsulated' means that less than 10%, 20%, 30%, 40%, 50%, 60% or less of the composition containing the therapeutic agent of the invention can be sealed, enclosed or encased within the capsule. Advantageously, encapsulation can be determined by measuring the escape or activity of the composition containing the therapeutic agent of the invention using fluorescence and/or electron micrographs. For example, at least 1%, 5%, 10%, 20%, 30%, 40%, 50%, 60%, 70%, 80%, 90%, 99%, 99.9% of the composition containing the therapeutic agent is encapsulated in the capsule.

Aspects of the present disclosure are directed to a capsule, fabricated by a FDM 3D printing process. The capsule includes a core (including a therapeutic agent) and a shell (printed as a composite material). The FDM 3D printing process is used to prepare polyvinyl alcohol (PVA) based capsule shells, where the capsule shell is filled with the therapeutic agent, as a liquid composition. The liquid composition is later solidified at room temperature. The therapeutic agent from the capsule is released following administration.

The method of the present disclosure obviates the need for expensive equipment and overcomes the drawbacks of the art by providing medicine that is personalized to each patient. A pharmacist or a healthcare practitioner can fill the shell with a composition (including the therapeutic agent), in required doses, by warming the composition till it becomes a liquid, gel or suspension, and then fill the shell with the composition using syringes, droppers, or pipettes, allowing accurate dosage adjustment. The method can be used to dispense various drugs that suffer from drawbacks such as poor solubility and bioavailability in precise dosage amounts customized to the needs of individual patients. Although the present disclosure relates to the use of this technology to produce the capsule, most particularly in relation to pharmaceuticals, a skilled person will readily appreciate that the principles of the present disclosure are readily applicable to nutraceuticals and food supplements, as well.

FIG. 1 illustrates a schematic flow chart of a method 100 for producing a core-shell capsule for delivering a therapeutic agent. The order in which the method 100 is described is not intended to be construed as a limitation, and any number of the described method steps can be combined in any order to implement the method 100. Additionally, individual steps may be removed or skipped from the method 100 without departing from the spirit and scope of the present disclosure.

At step 102, the method 100 includes printing a composite material via a nozzle on a substrate while moving the nozzle in a pre-designed pattern to create the shell of a hollow capsule. In an embodiment, the shell of the hollow capsule is printed via a FDM 3D printer. The FDM 3D printer includes three parts—a nozzle, a substrate, and a movable stage to support the substrate. The FDM 3D printer communicates with a communications interface coupled to a computing device, to create the shells from a 3D model/CAD model.

The composite material (including one or more thermoplastic polymers), in the form of plastic threads or filaments, is fed into the nozzle. The nozzle is generally heated to a pre-defined temperature. In some embodiments, the temperature at which the nozzle is pre-heated is based on the thermoplastic polymer and the 3D object to be made. For example, in some embodiments, the nozzle is operated at a temperature range of 50 to 400° C., preferably 80 to 380° C., and yet more preferably 120 to 200° C. In a preferred embodiment, the nozzle is pre-heated to a temperature of 200° C. (Table 1). The nozzle has one or more output openings through which the composite material (that is, in the form of filaments or plastic threads) is extruded. In some embodiments, the output opening has a diameter of 0.05 to 4 millimeters (mm), preferably 0.1 to 3 mm, and more preferably 0.1 to 1 mm, and yet more preferably of about 0.4 mm (Table 1). Other ranges are also possible.

In some embodiments, a conveyor is deployed for conveying the composite material and any optional one or more further composite materials to and/or through the nozzle. Suitably the conveyor grips the relevant filament and feeds it through itself towards and/or through the relevant nozzle. Suitably the conveyor is controlled to deliver the relevant filament at a rate and/or at intervals suitable to provide the desired solid dosage form. The conveyor, or a part thereof (e.g. "a feeder") may be heated, suitably via a heating element associated therewith, optionally a separate and/or separately controllable heating element from any heating elements associated with the nozzle.

The composite material is further printed on the substrate by moving the nozzle in a pre-designed pattern to create the shell of the hollow capsule. As used herein, the term 'pre-designed pattern' may refer to the digital 3D model/CAD model or the design controlled by the computing device. In an embodiment, the substrate is cardboard covered with paper tape, which promotes the adhesion of the shell to the substrate during the printing process. In a preferred embodiment, the shell may be removable from the substrate following its production. In some embodiments, the substrate can be one or more of a plastic sheet, a metal sheet, a timber board, and a chipboard sheet.

The substrate is further supported by the movable stage. The movable stage is a flat surface that supports the shell form throughout the printing process. In an embodiment, the movable stage is operated at a temperature of 30 to 120° C., preferably 40 to 100° C., more preferably 50 to 80° C., and yet more preferably at about 60° C. (Table 1). The low surface temperature of the movable stage facilitates cooling or hardening to improve the final structure of the printed shell. Other ranges are also possible.

The shell may be printed by moving the nozzle, and the movable stage in multiple directions −X, Y, and Z (based on the pre-defined digital 3D model/CAD model). The FDM 3D printer allows for precise control of the amount of the composite material and the location of the deposit to shape each layer. After completing one layer, the printer's nozzle is lowered for the next layer of the composite material to be added to the first layer. For example, the first layer formed in the present disclosure have a height in a range of 0.05 to 0.5 mm, preferably 0.1 to 0.4 mm, preferably 0.15 to 0.3 mm, or even more preferably about 0.27 mm, as shown in Table 1. In a further preferred embodiment, the other layers formed in the present disclosure have heights in a range of 0.05 to 0.5 mm, preferably 0.1 to 0.4 mm, preferably 0.15 to 0.3 mm, or even more preferably about 0.27 mm. or even more preferably about 0.18 mm, as shown in Table 1. The count of layers used to form the shell may vary based on the dimension of the 3D object. In one embodiment, the shell of the capsule has at least 1 layer, preferably at least 2 layers, preferably at least 4 layers, or even more preferably at least 8 layers. Other ranges are also possible.

The FDM 3D printer has the communications interface coupled to the computing device, and the FDM 3D printer removably retains the computing device. The computing device stores, retrieves, and processes the pre-designed pattern. The FDM 3D printer is operable via the computing device, more particularly, the computing device running by software, based on user inputs, data files, and databases.

The shell defines a cavity within the hollow capsule, and the shell has an opening at an apex of an outer surface of the shell. In some embodiments, the shell of the hollow capsule is in the shape of an ovoid that widens from a top end to a bottom end, opposite the top end. There are several advantages of the oval shape of the shell. The ovoid shell shape with an open top dome allows for efficient filling of the shell with a syringe or pipette without needing another step to seal the shell. The dome shape gives a better surrounding support of a filled composition inside the shell and less direct contact with the composition when a pharmacist or a patient handles the dosage form. One of the advantages of the ovoid shape is that it allows the accommodation of a desired volume of the composition to fill in the shell. In some embodiments, the shell may also exist in other forms, such as a conical shape, a cubical shape, a torus shape, a cylindrical shape, a disc shape, an ellipse shape, and a cuboidal shape. In some embodiments, the average width of the opening is from about 1/20 to about 4/5, preferably 3/20 to 7/10, preferably 1/4 to 3/5, preferably 7/20 to 9/20 of an average maximum diameter of the shell. In some embodiments, the average thickness of the shell is from about 0.5 mm to 1 mm, more preferably from about 0.6 mm to 0.9 mm. For example, a shell printed in the present disclosure has a thickness of about 0.8 mm (Table 1). The shape, count, and size of the shell opening or the shell itself may be changed per the customized needs. Other ranges are also possible.

Various parameters, such as print speed, travel speed, fill pattern, etc., can be adjusted during the shell preparation process. In some embodiments, the printing is operated at a condition having a print speed in a range of 10 to 120 millimeters per second (mm/sec), more preferably 20 to 100 mm/sec, and yet more preferably 50 to 80 mm/sec. For example, the printing of the present disclosure is operated at a speed of 60 mm/sec (Table 1). As used herein, "print speed" refers to the rate at which the FDM 3D printer moves when extruding the filament (composite material). Other ranges are also possible.

In some embodiments, the printing is further operated at a travel speed of 10 to 200 mm/sec, more preferably 20 to 150 mm/sec, and yet more preferably 50 to 80 mm/sec. For example, the printing of the present disclosure is operated at a travel speed of 100 mm/sec (Table 1). Travel speed is the moving speed of the FDM 3D printer during non-printing status without squeezing the printing material out of the nozzle. Other ranges are also possible.

The printing is operated at a full density of at least 5%. For example, the printing of the present disclosure is operated at a full density of 15% (Table 1). In some embodiments, the printing is operated at the condition of having at least one fill pattern selected from the group consisting of a linear fill pattern, a triangular fill pattern, a diagonal fill pattern, and a hexagonal fill pattern. In some embodiments, the fill pattern may include, but are not limited to, an octet fill pattern, a concentric fill pattern, a tri-hexagonal fill pattern, a cubic fill pattern, a cross fill pattern, a grid fill pattern, and a gyroid fill pattern. For example, the printing of the present disclosure is operated at the condition of having the hexagonal fill pattern (Table 1). The various printing parameters used during the fabrication of the shell are provided in Table 1.

TABLE 1

| Printing parameters during the fabrication of the shell | | |
|---|---|---|
| Category | Parameter | Printing conditions |
| Printing | Nozzle size | 0.4 mm |
| Printing | Extruder temperature/printing temperature | 200° C. |
| Printing | Movable stage temperature | 60° C. |
| Layer | Start/bottom layer | 2 |
| Layer | End/top layer | 2 |
| Layer | Layer height | 0.18 mm |
| Layer | First layer height | 0.27 mm |
| Layer | Print speed | 60 mm/sec |
| Layer | Travel speed | 100 mm/sec |
| Shell | Shell count | 2 |
| Shell | Shell thickness | 0.8 mm |
| Infill | Fill density | 15% |
| Infill | Fill pattern | Hexagonal |

In some embodiments, the composite material includes a thermoplastic polymer, a plasticizer, and a filler. In some embodiments, the thermoplastic polymer includes one or more selected from the group consisting of a polyacrylate, a silicone, a polyurethane, a polyolefin, a polyalkylene glycol, a polyvinyl alcohol, a polyamide, an acrylonitrile butadiene styrene, a polylactic acid, a polyglycolide, a nylon, or a co-polymer thereof, and a mixture thereof. Suitable examples include, but are not limited to, polyethylene, polypropylene, polyvinyl chloride, polystyrene, polybenz-imidazole, acrylic, and Teflon™. In a preferred embodiment, the thermoplastic polymer used in the composite material is polyvinyl alcohol. The polyvinyl alcohol filament is chosen to fabricate the shell as it is a biocompatible, hydrophilic polymer exhibiting good adhesion properties and thermal stability. In some embodiments, the polyvinyl alcohol filament has a viscosity of no more than 50 mPa·s, suitably no more than 30 mPa·s, suitably no more than 10 mPa·s, though suitably having a viscosity of at least 1 mPa·s, most suitably a viscosity between 2 and 8 mPa·s. In some embodiments, the polyvinyl alcohol filament has a molecular weight of 10,000-300,000 g/mol, preferably 30,000-250,000 g/mol, preferably 50,000-200,000 g/mol, preferably 70,000-150,000, or even more preferably about 90,000-100,000 g/mol. In some embodiments, 80-99.9% of the polyvinyl alcohol filament is hydrolyzed, preferably 85-99%, preferably 90-98%, or even more, preferably about 97% of the polyvinyl alcohol filament is hydrolyzed. Moreover, polyvinyl alcohol is a safe pharmaceutical excipient for drug delivery applications listed in the United States and European Pharmacopoeia. Other ranges are also possible.

One of the critical factors to consider in the 3D printing process is glass transition temperature ($T_g$), as it determines the temperature at which the polymer changes to a viscous state. In some embodiments, the composite material includes a thermoplastic polymer having a glass transition temperature ($T_g$) greater than or equal to 30° C., particularly in a range of 35-100° C. It is also desirable to use a thermoplastic polymer that makes the composite material desirable for the FDM 3D printing process, for consistent printing, without causing any distortions. Other ranges are also possible.

The plasticizer imparts several desirable properties to the composite material, such as smoothness, flexibility, and fluidity on extrusion. Suitable examples of plasticizers may include, but are not limited to, triethyl citrate (TEC), glycerol, castor oil, oleic acid, glycerol, tryacetin and polyalkylene glycols (such as polyethylene glycol or polypropylene glycol, such as PEG 400). In some embodiments, combinations of the plasticizer may be used. For example, the combinations may include the conjugation of triacetin with cellulose-based carriers such as hydroxypropyl cellulose (HPC), hydroxypropylmethylcellulose (HPMC), and hydroxypropylmethylcellulose acetate succinate (HPMCAS); glycerol plasticizer in conjunction with poly(vinyl alcohol)-based carrier; triethyl citrate (TEC) in conjunction with acrylate, methacrylate, or copolymers.

The filler strengthens the composite material and thereby facilitates its generation and processing during the 3D printing. Suitable examples of the filler may include but are not limited to, plant cellulose, dibasic calcium phosphate, vegetable fats and oils, lactose, sucrose, glucose, mannitol, sorbitol, calcium carbonate, magnesium stearate, and microcrystalline cellulose.

The composite material may optionally include other excipients, such as, anti-adherents (magnesium stearate); binders (saccharides, polysaccharides or derivatives thereof, for example, starches, cellulose or modified cellulose such as microcrystalline cellulose and cellulose ethers such as hydroxypropyl cellulose, hydroxypropyl methyl cellulose, and derivatives thereof; sugar alcohols, for example, xylitol, sorbitol or maltitol; synthetic polymers, for example, polyvinylpyrrolidone (PVP), polyethylene glycol (PEG); disintegrants (crosslinked polyvinylpyrrolidone, crosslinked sodium carboxymethyl cellulose, croscarmellose sodium, modified starch sodium, or starch glycolate); lubricants (silica; fats, for example, vegetable stearin; and magnesium stearate or stearic acid); glidants (fumed silica, talc, magnesium carbonate, and colloidal silica); flavorants (complex volatile oil (anise oil), aldehyde (vanillin), ginger oil, peppermint oil, and lemongrass oil); preservatives (sodium benzoate, potassium sorbate, and methyl hydroxybenzoate (methylparaben)); sweeteners (such as acesulfame potassium, aspartame, glucose, dextrate, dextrose, fructose, mannitol, maltose, alitame, isomalt, saccharin, sorbitol, sucralose, and xylitol); and coatings (cellulose ether hydroxypropyl methylcellulose (HPMC) film coating); synthetic polymers, shellac, corn protein zein or other polysaccharides, gelatin; enteric coatings, for example, including fatty acids, waxes, shellac, plastics, plant fibres).

At step 104, the method 100 includes introducing the composition, in liquid form, containing the therapeutic agent at a temperature of at least 45° C. into the cavity of the hollow capsule via the opening of the shell. In some embodiments, the composition is introduced into the hollow capsule in a form selected from the group consisting of an emulsion, an oil solution, a dispersion, and a suspension.

In some embodiments, the composition is at least one liquid mixture selected from the group consisting of a self-nano emulsified drug delivery system (SNEDDS), a self-micro emulsifying drug delivery system (SMEDDS), and a self-emulsifying drug delivery system (SEDDS). In some embodiments, the liquid composition is mixed with water to form a nanoemulsion. In some embodiments, the nano-emulsion has an average particle size of 10 to 800 nanometers (nm), more preferably 50 to 700 nm, more preferably 150 to 600 nm, and yet more preferably 250 to 500 nm. Other ranges are also possible.

The composition includes the therapeutic agent and one or more pharmaceutically acceptable excipients or carriers, such as emulsifiers, fatty acids, etc. In some embodiments, the composition consists of 0.0001 to 50 wt. %, more preferably 10 to 35 wt. %, and yet more preferably 25 to 30 wt. %, of at least one therapeutic agent based on the total weight of the liquid composition. The therapeutic agent may be a drug, a protein, a peptide, a gene, a compound, or a pharmaceutically active ingredient. In some embodiments, the therapeutic agent is a drug with poor solubility or poor bioavailability—for example, cyclosporine.

A "therapeutic agent with poor solubility", meaning that the therapeutic agent may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. In general, it may be said that the drug has a dose-to-aqueous solubility ratio greater than 10 mL, and more typically greater than 100 mL, where the drug solubility is the minimum value observed in any physiologically relevant mixture (e.g., those with pH values between 1 and 8) including USP simulated gastric and intestinal buffers. Suitable therapeutic agents include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents.

In some embodiments, the composition further includes 5 to 60 wt. %, more preferably 10 to 40 wt. %, and yet more preferably 20 to 35 wt. %, of at least one solvent based on the total weight of the liquid composition. At least one solvent is selected from the group consisting of diethylene glycol monoethyl ether, polyethylene glycol 200, polyethylene glycol 400, polyethylene glycol 6000, propane-1,2,3-triol, polypropylene glycol, propylene glycol, 2-pyrrolidone, tetraethylene glycol, diethylene glycol monoethyl ether, and a mixture thereof.

The composition further includes 5 to 25 wt. %, more preferably 10 to 20 wt. %, and yet more preferably 15 to 18 wt. %, of at least one fatty acid based on the total weight of the liquid composition. At least one fatty acid is selected from the group consisting of heptanoic acid, octanoic acid, nonanoic acid, decanoic acid, and a mixture thereof. The fatty acid may include, but are not limited to, arachidonic acid, α-linolenic acid, linoleic acid, lauric acid, myristic acid, palmitic acid, palmitoleic acid, stearic acid, and oleic acid.

The composition includes 15 to 55 wt. %, more preferably 20 to 45 wt. %, and yet more preferably 35 to 40 wt. %, of at least one emulsifier based on the total weight of the liquid composition. At least one emulsifier is selected from the group consisting of caprylate, caprate monoglyceride, caprate diglyceride, glyceryl monocaprylate, propylene glycol monocaprylate, lauroyl glyceride, stearoyl glyceride, sorbitan monolaurate, sorbitan monooleate, sorbitan sesquioleate, sorbitan trioleate, glyceryl monostearate, hydrogenated castor oil, polysorbate, polyethylene glycol, polyethylene glycol ester, glycerol ester, polyvinylpyrrolidone, and a mixture thereof. In some embodiments, the emulsifier may be a primary or a secondary emulsifier. The primary emulsifier includes a lower hydrophilic-lyophilic balance (HLB) with respect to the secondary emulsifier. In some embodiments, the primary emulsifier may include, but is not limited to, span 60, span 85, span 65, span 40, span 20, and sorbitan oleate (span 80). In some embodiments, the secondary emulsifier may include but is not limited to, Triton™ X-100, Tween™ 80, Tween™ 20, Tween™ 40, Tween™ 60, Tween™ 85, OP4, and OP 7. Other ranges are also possible.

The composition may also include other excipients such as coloring agents (such as tartrazine), compression aids, antioxidants (such as sodium metabisulphite, propyl gallate), and granulating agents.

In a preferred embodiment, the composition includes 0.01 to 20 wt. %, more preferably 5 to 15 wt. %, and yet more preferably 10 to 12 wt. %, of cyclosporin A (CyA/CsA) based on the total weight of the liquid composition. The CyA/CsA is an immunosuppressive agent used to reduce the rejection rate in organ transplants and treat several autoimmune diseases. The drug has poor aqueous solubility and incomplete oral absorption with high inter-subject variability, leading to drug-associated nephrotoxicity. There is an increased need to improve the solubility and dispense the drug in personalized doses tailored to the patient profile. Although the description provided here refers to the use of the CyA/CsA, it may be understood to a person skilled in that art that the CyA/CsA may be replaced by other poorly soluble drugs/drugs with poor bioavailability, as may be obvious to a person skilled in the art. The SNEDDS method enhances the solubility of the CyA/CsA. Other ranges are also possible.

In some embodiments, the composition further includes 5 to 25 wt. %, more preferably 5 to 15 wt. %, and yet more preferably 10 to 12 wt. %, of propylene glycol monocaprylate based on the total weight of the liquid composition. In an embodiment, 15 wt. % of Capryol™ 90 is used. The composition further includes 10 to 30 wt. %, more preferably 15 to 25 wt. %, and yet more preferably 20 to 22 wt. %, of polyoxyl 35 hydrogenated castor oil based on the total weight of the liquid composition. The polyoxyl 35 castor oil is a polyethylene glycol derivative of hydrogenated castor oil with an average PEG chain length of 35. PEG-35 hydrogenated castor oil is a nonionic surfactant used as an emulsifying and solubilizing agent in pharmaceutical preparations and cosmetics. The composition further includes 1 to 20 wt. %, more preferably 5 to 15 wt. %, and yet more preferably 10 to 12 wt. %, of polyethylene glycol 400 based on the total weight of the liquid composition. Polyethylene glycol 400 is a low-molecular-weight grade of polyethylene glycol with low-level toxicity. In addition, polyethylene glycol 400 is very hydrophilic, which renders it a useful ingredient in drug formulations to augment the solubility and bioavailability of weakly water-soluble drugs. The composition further includes 30 to 50 wt. %, more preferably 35 to 45 wt. %, and yet more preferably 37 to 40 wt. %, of polyethylene glycol 6000 based on the total weight of the liquid composition. The main advantage of polyethylene glycol 6000 is that it is used as a solidifying agent for the composition. The polyethylene glycol 6000 is liquid at temperatures around 45° C. and solidifies at room temperature. The composition further includes 5 to 25 wt. %, more preferably 5 to 15 wt. %, and yet more preferably 10 to 12 wt. %, of octanoic acid based on the total weight of the liquid composition. Other ranges are also possible.

In an embodiment, the composition of the desired SNEDDS is listed in Table 2.

TABLE 2

| S. No. | Ingredients of liquid SNEDDS | Composition % |
|---|---|---|
| 1 | Capryol 90 | 15 |
| 2 | Octanoic Acid | 15 |
| 3 | Cremophore EL | 20 |
| 4 | PEG-400 | 10 |
| 5 | PEG 6000 | 40 |

At step 106, the method 100 includes naturally cooling the composition inside the shell to solidify the composition and adhere the composition to the inner surface of the shell, thereby forming a core of the core-shell capsule. In some embodiments, the composition is cooled at room temperature to form the core. In some embodiments, the core is at least partially enclosed within the shell. In some further embodiments, at least 50%, preferably at least 60%, preferably at least 70%, preferably at least 80%, preferably at least 85%, preferably at least 90%, preferably at least 95%, or even more preferably at least 99% or more of the composition containing the therapeutic agent is enclosed and adhered to the inner surface of the shell, thereby forming the core of the core-shell capsule. In some further embodiments, at least 50 wt. %, preferably at least 60 wt. %, preferably at least 70 wt. %, preferably at least 80 wt. %, preferably at least 85 wt. %, preferably at least 90 wt. %, preferably at least 95 wt. %, or even more preferably at least 99 wt. % or more of the composition containing the therapeutic agent is enclosed and adhered to the inner surface of the shell, based on a total weight of the core. In some further preferred embodiments, at least 50 vol. %, preferably at least 60 vol. %, preferably at least 70 vol. %, preferably at least 80 vol. %, preferably at least 85 vol. %, preferably at least 90 vol. %, preferably at least 95 vol. %, or even more preferably at least 99 vol. % or more of the composition containing the therapeutic agent is enclosed and adhered to the inner surface of the shell, based on a total volume of the core. The concentration of the therapeutic agent in the core of the core-shell capsule and the concentration of the therapeutic agent in the composition in liquid form while introducing the composition into the shell of the capsule, are the same. The core-shell capsule stabilizes the therapeutic agent prior to administration and releases the therapeutic agents from the capsule following administration.

In an embodiment of the invention, the composition containing the therapeutic agent is added to the cavity in layers, each layer corresponding with a composition having a concentration of the therapeutic agent different from the concentration of the therapeutic aged in the composition added in a prior layer. In this manner the release of the therapeutic agent can be further controlled after ingestion by a patient. For example, for fast release of the therapeutic agent from the cavity, and/or release of a pre-dose, the last layer (i.e., the uppermost layer that is exposed at the opening of the capsule) may have a high concentration of the therapeutic agent. Dissolution of this portion of the composition, and thus release of a pre-dose of the therapeutic agent, may occur prior to complete degradation and/or dissolution of the shell of the hollow capsule.

In a preferred embodiment, the liquid composition is added to the cavity which is subjected to spinning while the composition is in liquid form and remains spinning while the composition cools and solidifies. Spinning may be conducted, for example on a spin coater, such that the composition distributes upwards along the inner surface of the capsule wall. In this matter, the release of the therapeutic agent is further controllable and customizable. In effect, this strategy forms one or more cups of the composition inside the capsule with the cup having a cavity that may be filled later with the same or a different composition. The cup cavity can then be filled with a composition containing a therapeutic agent in a different concentration than the composition that is first added and subjected to spin coating or spinning.

A pharmaceutical formulation includes the core-shell capsule prepared by method 100 is described. The core-shell capsule contains an effective amount of the therapeutic agent to treat a subject. Effective amount means the amount of the therapeutic agent that, when administered to a subject for treating a disease, is sufficient to affect such treatment for the disease. The 'effective amount' can vary depending on the therapeutic agent, the intention of treatment vis-a-vis prevention, prophylaxis, intent-to-treat, treatment, the disease and its severity, and the age, comorbidity, weight, gender, social habits such as smoking, alcohol consumption, etc., of the subject to be treated. The subject is a mammal. In some embodiments, the subject is a human.

EXAMPLES

The following examples describe and demonstrate exemplary embodiments of the method 100 for producing the core-shell capsule for delivering the therapeutic agent described herein. The examples are provided solely for the purpose of illustration and are not to be construed as limitations of the present disclosure, as many variations thereof are possible without departing from the spirit and scope of the present disclosure.

FIGS. 2A-2F show an exemplary flow chart of the production of personalized medicine using the 3D printing. FIG. 2A shows an AutoCAD design of the shell of the capsule. The shells have specific diameters and open sizes to accommodate the desired volume of the filled drug formulation. The shells are printed on the surface of cardboard covered with paper tape to stabilize the printed shells. The shells are arranged to make the shells look like a tablet strip.

The liquid formulation that contains the drug and the needed excipients are prepared at 45° C. The liquid formulation is then filled, using a syringe, inside the printed shells through the hole at the top of the shell dome (FIG. 2D). The filled formulation solidifies at room temperature to form one piece with the shell (FIG. 2E). The dose is adjusted through the amount of liquid formulation filled inside the shell (FIG. 2F).

Figure 3:
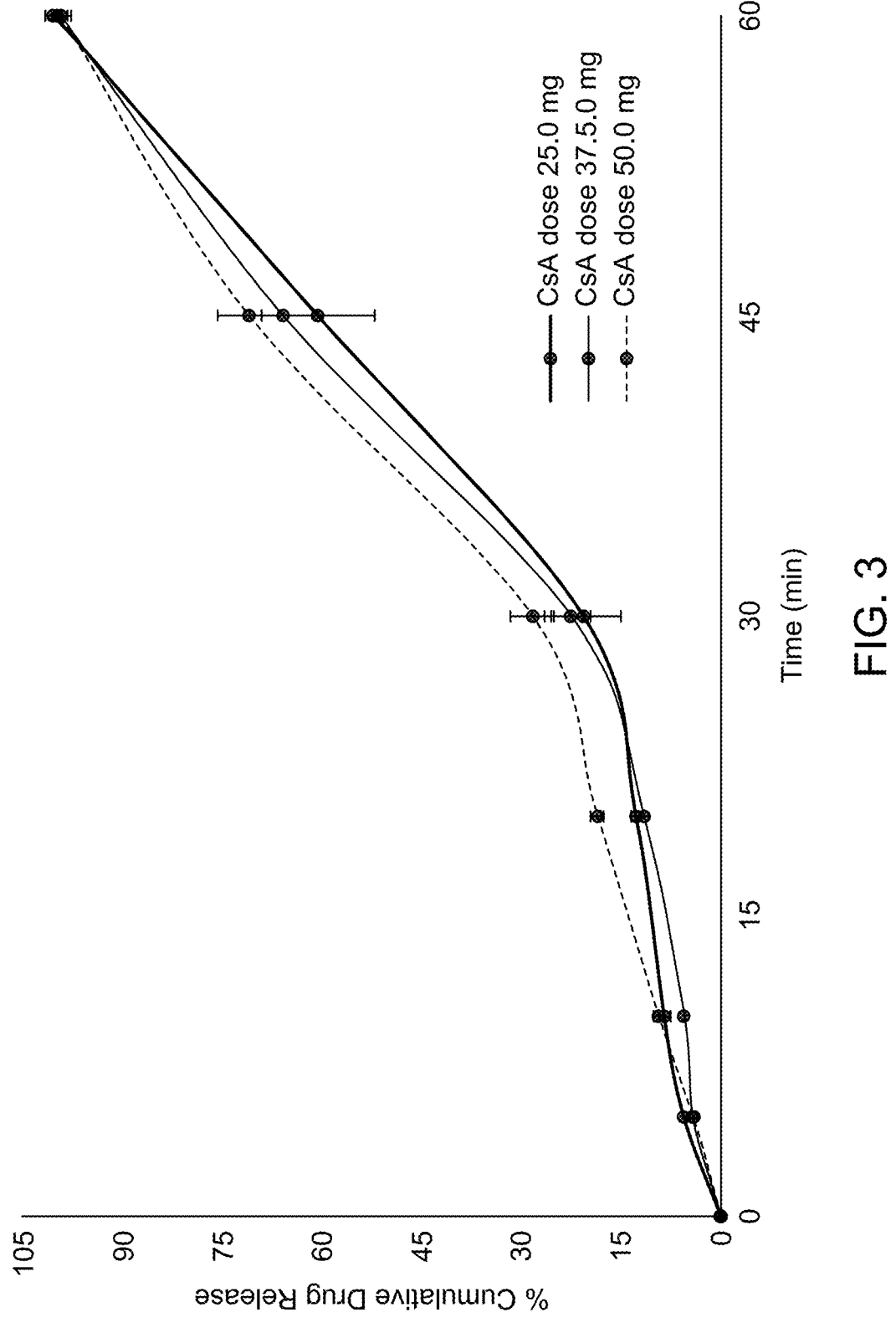
FIG. 3 is a graph depicting a drug release profile of core-shell capsules carrying various doses of cyclosporin A (CyA/CsA), according to certain embodiments of the present disclosure.

FIG. 3 is a graph depicting the drug release profile of core-shell capsules carrying various doses of cyclosporin A (CyA/CsA). For this purpose, a dissolution study was conducted using a USP dissolution Type I apparatus (Basket type). The analysis was conducted at 100 rotations per minute (rpm) under sink conditions using a phosphate buffer of pH 6.8 as a dissolution media. A complete release of all CsA doses was achieved within 60 minutes. From FIG. 3, it can be observed that the decreasing order of the cumulative drug release is as follows: CsA dose 50 milligrams (mg) >CsA dose 37.5 mg>CsA dose 25 mg.

The core-shell capsules produced by the method of the present disclosure provide personalized medicine, a promising solution to the problems associated with dispensing mass-produced medication, such as sub-therapeutic efficacy and toxicity. One of the advantages of the present disclosure is that there is no need for extensive experience with 3D printing. A pharmacist or a healthcare practitioner can fill the shells with the drug formulation using syringes or pipettes, allowing accurate dosage adjustment. Also, various doses of the same drug can be dispensed to the patient without wasting the formulation. The method of the present disclosure can be adapted to dispense various drugs that suffer from challenges such as poor absorption/solubility.

Numerous modifications and variations of the present disclosure are possible in light of the above teachings. It is therefore to be understood that within the scope of the appended claims, the invention may be practiced otherwise than as specifically described herein.

The invention claimed is:

1. A method for producing a core-shell capsule for delivering a therapeutic agent, comprising:
   printing a composite material via a nozzle on a substrate while moving the nozzle in a pre-designed pattern to create a shell of a hollow capsule, wherein the shell defines a cavity within the hollow capsule and the shell has an opening at an apex of an outer surface of the shell;
   wherein the shell of the hollow capsule is in a shape of an ovoid that widens from a top end to a bottom end opposite to the top end;
   wherein an average width of the opening is from about 1/20 to about 4/5 of an average maximum diameter of the shell;
   wherein during the printing, the substrate is supported on a movable stage, and wherein the movable stage can move in multiple directions;
   introducing a composition, in liquid form, containing the therapeutic agent at a temperature of at least 45° C. into the cavity of the hollow capsule via the opening of the shell, and naturally cooling the composition inside the shell to solidify the composition and adhere the composition to an inner surface of the shell thereby forming a core of the core-shell capsule;
   wherein the core is at least partially enclosed within the shell; and
   wherein a concentration of the therapeutic agent in the core of the core-shell capsule and the concentration of the therapeutic agent in the composition in liquid form during the introducing are the same,
   wherein the composition comprises:
      0.01 to 20 wt. % of cyclosporin A (CyA);
      5 to 25 wt. % of propylene glycol monocaprylate;
      10 to 30 wt. % of polyoxyl 35 hydrogenated castor oil;
      1 to 20 wt. % of polyethylene glycol 400;
      30 to 50 wt. % of polyethylene glycol 6000; and
      5 to 25 wt. % of octanoic acid, wherein each wt. % is based on a total weight of the liquid composition.

2. The method of claim 1, wherein the composite material comprises a thermoplastic polymer having a glass transition temperature ($T_g$) of greater than or equal to 30° C.

3. The method of claim 1, wherein the composite material comprises one or more thermoplastic polymers selected from the group consisting of a polyacrylate, a silicone, a polyurethane, a polyolefin, a polyalkylene glycol, a polyvinyl alcohol, a polyamide, an acrylonitrile butadiene styrene, a polylactic acid, a polyglycolide, a nylon, a co-polymer thereof and a mixture thereof.

4. The method of claim 1, wherein the composite material comprises at least one plasticizer, and at least one filler.

5. The method of claim 1, wherein the printing is operated at a condition having:
   a print speed in a range of 10 to 120 millimeters per second (mm/sec);
   a travel speed in a range of 10 to 200 mm/see;
   a full density of at least 5%; and
   at least one fill pattern selected from the group consisting of a linear fill pattern, a triangular fill pattern, a diagonal fill pattern, and a hexagonal fill pattern.

6. The method of claim 1, wherein the nozzle:
   is operated at a temperature in a range of 50 to 400° C.; and
   has an output opening having a diameter in a range of 0.05 to 4 millimeters (mm).

7. The method of claim 1, wherein the movable stage is operated at a temperature of 30 to 120° C.

8. The method of claim 1, wherein the shell of the hollow capsule is printed via a fused deposition modelling (FDM) 3D printer.

9. The method of claim 8, wherein the FDM 3D printer has a communications interface coupled to a computing device, and the FDM 3D printer removably retains the computing device, and wherein the computing device stores, retrieves, and processes the pre-designed pattern.

10. The method of claim 1, wherein the composition is introduced into the hollow capsule in a form selected from the group consisting of an emulsion, an oil solution, a dispersion, and a suspension.

11. The method of claim 1, wherein the composition is at least one liquid mixture selected from the group consisting of a self-nanoemulsified drug delivery system (SNEDDS), a self-microemulsifying drug delivery system (SMEDDS), and a self-emulsifying drug delivery system (SEDDS).

12. The method of claim 1, further comprising:
   mixing the composition, in liquid form, with water to form a nanoemulsion, wherein the nanoemulsion has an average particle size in a range of 10 to 800 nanometers (nm).

13. The method of claim 1, wherein the core-shell capsule stabilizes the therapeutic agent prior to administration and releases the therapeutic agent from the capsule following administration.

* * * * *